(12) United States Patent
Hagemeyer et al.

(10) Patent No.: US 6,191,312 B1
(45) Date of Patent: Feb. 20, 2001

(54) PROCESS FOR THE CATALYTIC OXIDATION OF 1,5-DIALKYLBICYCLO (3.2.1)OCTAN-8-OL TO GIVE 1,5 DIALKYLBICYCLO(3.2.1)OCTAN-8-ONE

(75) Inventors: Alfred Hagemeyer, Rheine; Rolf Peter Schulz, Frankfurt; Harald Werner, Bad Homburg; Uwe Dingerdissen, Seeheim-Jugenheim; Klaus Kühlein, Kelkheim; Heinz Alexander, Frankfurt, all of (DE)

(73) Assignee: Aventis Research & Technologies GmbH & Co. KG, Frankfurt (DE)

( * ) Notice: Under 35 U.S.C. 154(b), the term of this patent shall be extended for 0 days.

(21) Appl. No.: 09/368,081

(22) Filed: Aug. 3, 1999

(30) Foreign Application Priority Data

Aug. 5, 1998 (DE) .............................. 198 35 323

(51) Int. Cl.⁷ .................................. C07C 49/105
(52) U.S. Cl. ..................... 568/374; 568/367; 568/361
(58) Field of Search .................... 568/357, 360, 568/361, 367, 374; 502/209, 211, 312

(56) References Cited

U.S. PATENT DOCUMENTS

| | | | |
|---|---|---|---|
| 3,860,635 | * 1/1975 | Kitchens | 560/256 |
| 3,928,246 | * 12/1975 | Stadler et al. | 512/15 |
| 4,100,197 | * 7/1978 | Jaedicke et al. | 568/364 |
| 4,146,574 | * 3/1979 | Onoada et al. | 423/299 |
| 5,091,354 | * 2/1992 | Ellis, Jr. et al. | 502/200 |

FOREIGN PATENT DOCUMENTS 2 441 604   6/1980   (FR) .

OTHER PUBLICATIONS

Fujibayashi et al. An Efficient Aerobic Oxidation of Various Organic Compounds Catalyzed by Mixed Addenda Heteropolyoxometalates Containing Molybdenum and Vanadium (1996).

Neumann et al. Selective Aerobic Oxidative Dehydrogenation of Alcohols and Amines Catalyzed by a Supported Molybdenum–Vanadium Heteropolyanion Salt Na5PMo2v2040. (1991).

CA:77:87478 abs of Bull Soc Chim Fr by Brun (5) pp. 1825–1834, 1972.*

CA:97:72234 abs of Tetrahedron Lett. by Becker 23(18) pp. 1883–1886, 1982.*

CA:84:42911 abs of J Am Chem Soc by Mueller 97(23) pp. 6862–6863, 1975.*

CA: 86:90097 abs of Arzneim.–Forsch. by Scheiber 26(10) pp. 1797–800, 1976.*

CA:101:210915 abs of J Pharm Sci by De la Cuesta et al 73(9) pp. 1307–1309, 1984.*

* cited by examiner

*Primary Examiner*—Jean F. Vollano
(74) *Attorney, Agent, or Firm*—Frommer Lawrence & Haug LLP

(57) ABSTRACT

A process for preparing a bicyclooctanone, in particular 1,5-dialkylbicyclo[3.2.1]octan-8-one, by reacting a bicyclooctanol, in particular dialkylbicyclo[3.2.1]octan-8-ol, with a. a catalyst applied to an active-carbon support and comprising heteropolyoxometallate anions of vanadium, molybdenum and phosphorus, and also a corresponding alkali-metal, alkaline-earth-metal and/or ammonium counter ion, and b. a gaseous, oxygen-containing oxidizing agent.

13 Claims, 6 Drawing Sheets

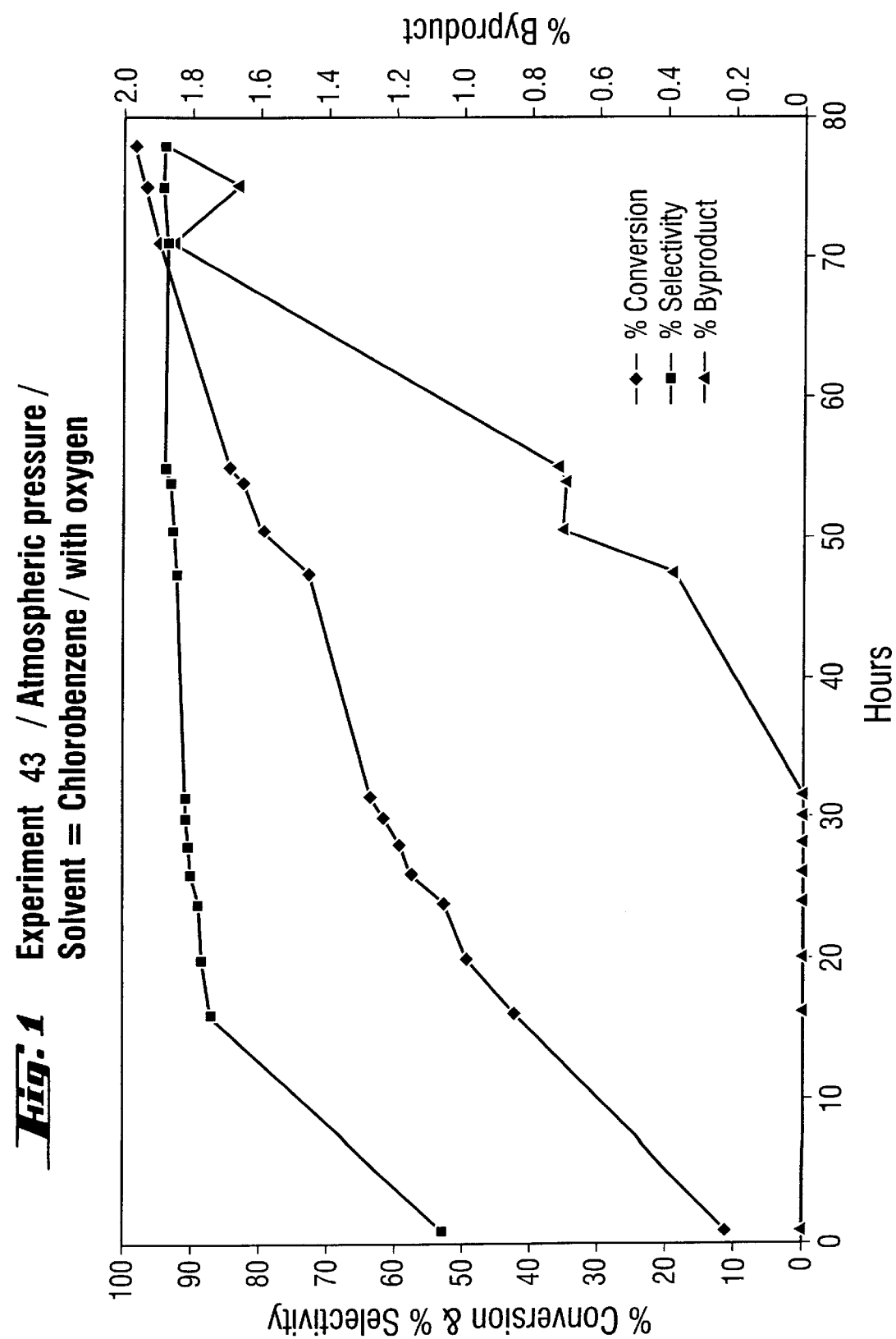
Fig. 1 Experiment 43 / Atmospheric pressure / Solvent = Chlorobenzene / with oxygen

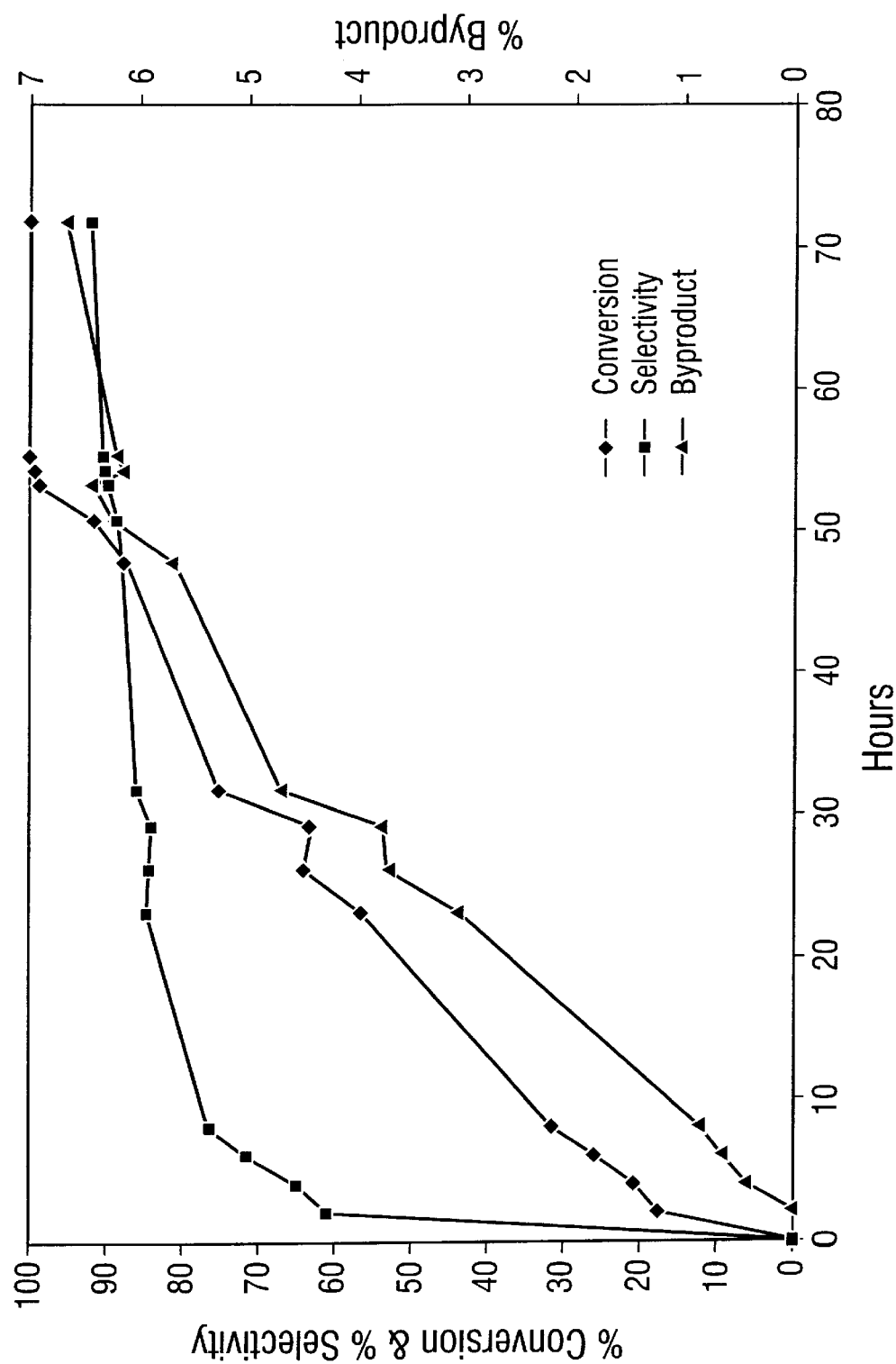
*Fig. 2* Experiment 98 / Atmospheric pressure / Solvent = Butyl acetate / with oxygen

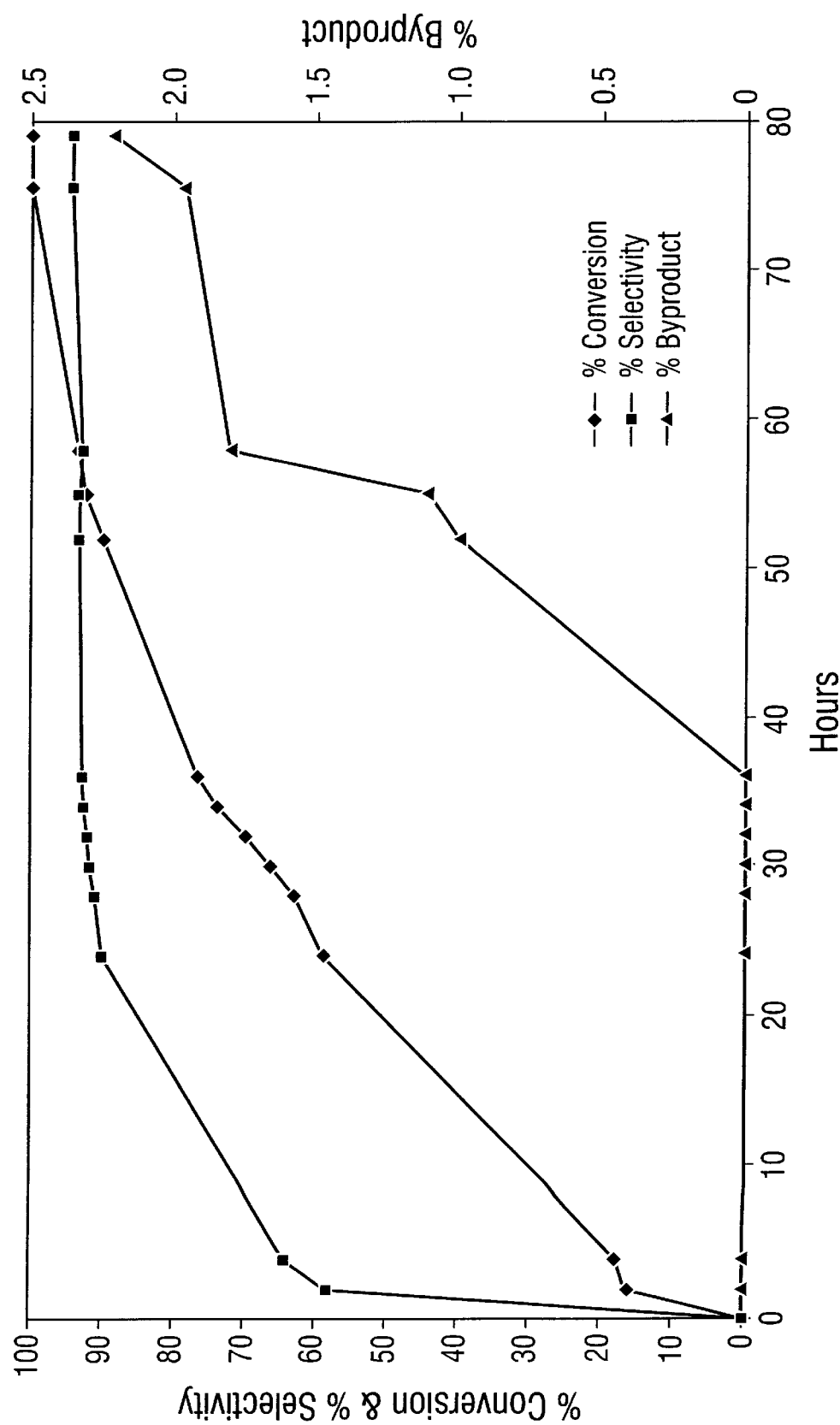
Fig. 3 Experiment 61 / Atmospheric pressure / Solvent = Chlorobenzene / with synthetic air

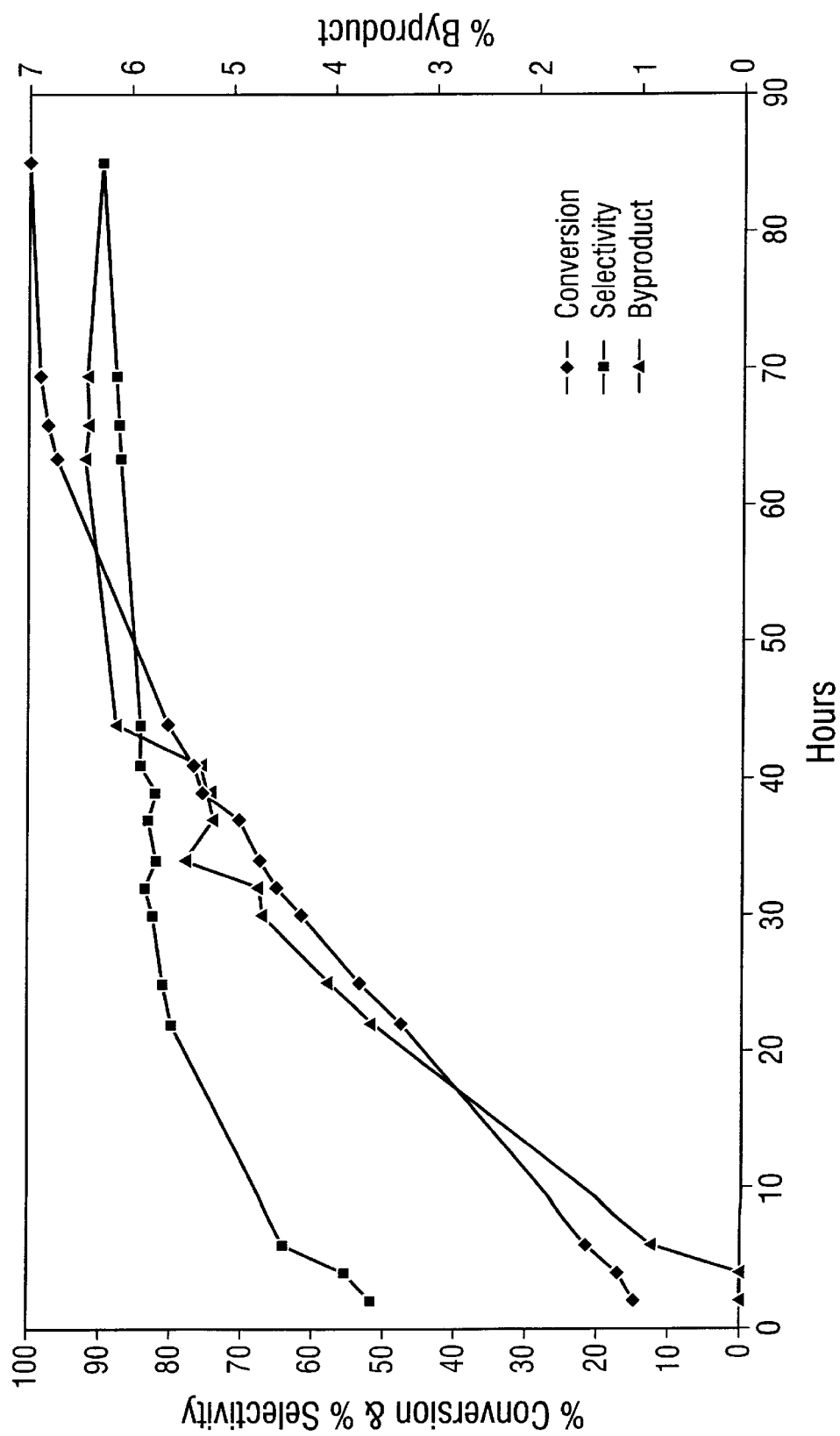
Fig. 4   Experiment 71 / Atmospheric pressure / Solvent = Butyl acetate / with synthetic air

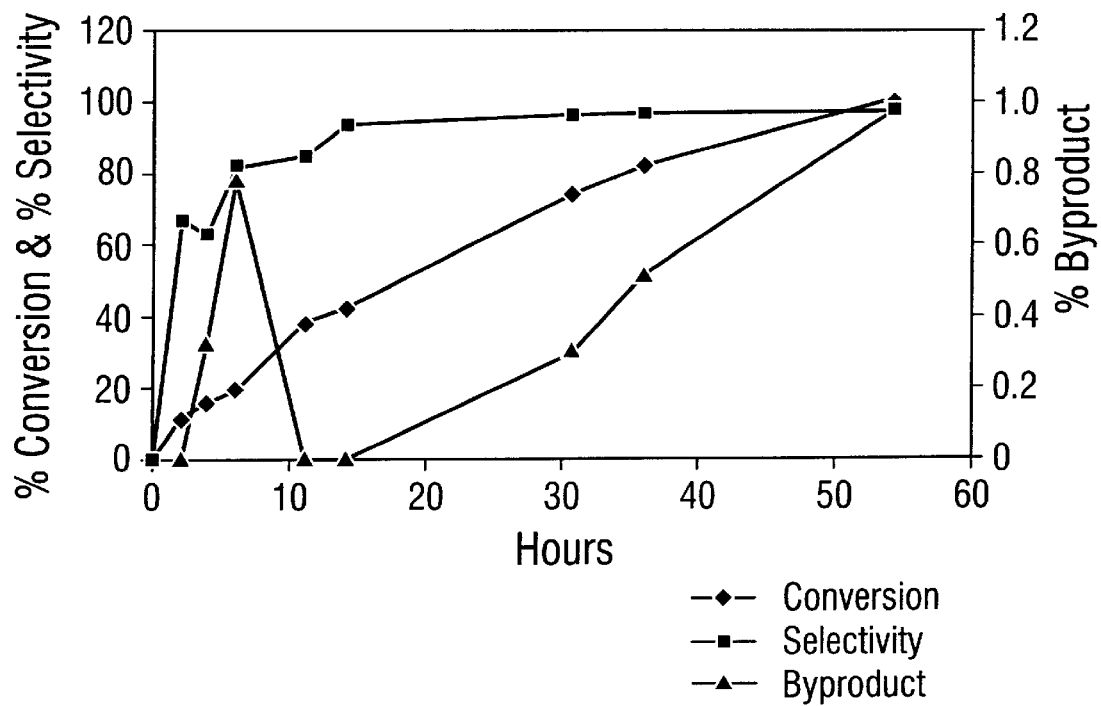
Fig. 5 Experiment 90 / Atmospheric pressure / Solvent = Chlorobenzene / with synthetic air
| Hours | Conversion | Selectivity | Byproduct |
|---|---|---|---|
| 0 | 0 | 0 | 0 |
| 2 | 11,7 | 67,09 | 0 |
| 4 | 16,36 | 62,53 | 0,33 |
| 6 | 18,81 | 81,77 | 0,79 |
| 11 | 38 | 84,50 | 0 |
| 14 | 41,97 | 92,95 | 0 |
| 31 | 73,74 | 95,99 | 0,287 |
| 36,5 | 81,94 | 95,84 | 0,51 |
| 55 | 100 | 96,93 | 0,97 |

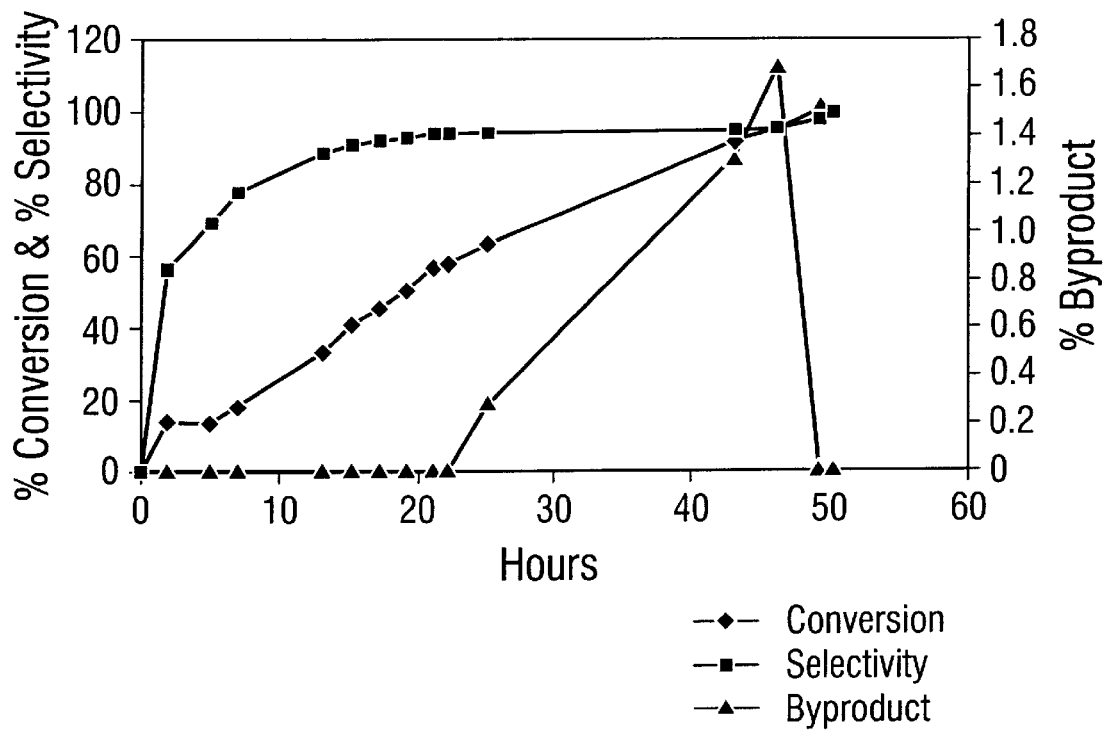
Fig. 6 Experiment 100 / Atmospheric pressure / Solvent = Chlorobenzene / with synthetic air
—♦— Conversion
—■— Selectivity
—▲— Byproduct
| Hours | Conversion | Selectivity | Byproduct |
|---|---|---|---|
| 0 | 0 | 0 | 0 |
| 2 | 13,67 | 55,08 | 0 |
| 5 | 13,18 | 67,91 | 0 |
| 7 | 18,5 | 77,03 | 0 |
| 13 | 32,48 | 87,55 | 0 |
| 15 | 39,85 | 89,76 | 0 |
| 17 | 44,94 | 90,88 | 0 |
| 19 | 49,78 | 91,9 | 0 |
| 21 | 56,2 | 92,83 | 0 |
| 22 | 56,76 | 92,76 | 0 |
| 25 | 62,29 | 93,16 | 0,26 |
| 43 | 91 | 93,75 | 1,3 |
| 46 | 94,81 | 94,78 | 1,65 |
| 49 | 100 | 96,998 | 0 |
| 50 | 100 | 100 | 0 |

PROCESS FOR THE CATALYTIC OXIDATION OF 1,5-DIALKYLBICYCLO (3.2.1)OCTAN-8-OL TO GIVE 1,5 DIALKYLBICYCLO(3.2.1)OCTAN-8-ONE

The present invention relates to a catalytic process for the selective oxidation of a bicyclooctanol to give a bicyclooctanone using an active-carbon-supported heteropolymetallate anion catalyst. In particular, the invention relates to oxidizing 1,5-dimethylbicyclo[3.2.1]octan-8-ol to the ketone using oxygen, oxygen-containing gases or air.

BACKGROUND OF INVENTION

Various processes are known for oxidizing secondary alcohols to give ketones. However, these conventional oxidation processes are associated with numerous disadvantages, e.g.

- the use of relatively expensive oxidizing agents in stoichiometric quantities or even in excess,
- the separation and disposal of used and unused oxidizing agent,
- the production of salts, creating disposal costs and making isolation of the product more difficult,
- high pressures,
- low selectivity, and
- lack of complete conversion.

Examples of known established processes are the Oppenauer oxidation using Al systems and the $H_2O_2$ oxidation using Ti, Mo and V systems, and transfer (de)hydrogenations.

The conventional processes are therefore frequently expensive and energy-intensive and burdened by considerable material separation problems in the isolation of the product from a complex reaction mixture. It is often difficult to dispose of oxidizing agents and auxiliary chemicals without harming the environment.

An object of the present invention was to provide a process for the selective oxidation of bicyclooctanols to the ketones which avoids the disadvantages of conventional oxidations, has low costs and is environmentally acceptable.

An oxidation process has now been found which uses an active-carbon-supported catalyst comprising a heteropolymetallate anion and which, under mild reaction conditions and even at atmospheric pressure, can use inexpensive oxidizing agents, such as oxygen-containing gases and even air,
and can achieve high conversions and even complete conversion with high selectivities
and without producing salts.

SUMMARY OF THE INVENTION

The present invention therefore provides a process for preparing a bicyclooctanone, in particular 1,5-dialkylbicyclo [3.2.1]octan-8-one, by reacting a bicyclooctanol, in particular 1,5-dialkylbicyclo[3.2.1]octan-8-ol, with a. a catalyst applied to an active-carbon support and comprising heteropolyoxometallate anions of vanadium, molybdenum and phosphorus, and also a corresponding alkali-metal, alkaline-earth-metal and/or ammonium counter ion, and b. a gaseous, oxygen-containing oxidizing agent.

BRIEF DESCRIPTION OF THE DRAWINGS

FIG. 1: Pure oxygen, clorobenzene

FIG. 2: Pure oxygen, butyl acetate

FIG. 3: Air, chlorobenzene

FIG. 4: Air, butyl acetate

FIG. 5: Air, chlorobenzene, 3-fold increase in catalyst quantity and starting material quantity FIG. 6: Scale-up in a 4 liter stirred flask (atmoshpere pressure, chlorobenzene, air)

DETAILED DESCRIPTION OF THE INVENTION

Alkyl are preferably, independently of one another, branched or unbranched methyl, ethyl, propyl, butyl, pentyl, hexyl or cyclohexyl radicals.

The oxidizing agent used comprises oxygen, oxygen-containing gases or air.

The novel oxidation can be carried out in the temperature range from 100 to 300° C., preferably from 120 to 250° C., and in the pressure range from 1 to 30 bar, preferably from 1 to 25 bar, in a variety of solvents or in bulk. In the case of the dimethyl compounds preferred conditions are from 140 to 250° C. and from 1 to 20 bar. The oxidizing agents used may comprise pure or diluted oxygen, in particular air or lean air. A particular embodiment of the present invention uses atmospheric pressure, and the oxygen-containing gas or air is introduced directly, either continuously or batchwise, with atmospheric pressure (or with the pressure drop produced through the reactor) via injection equipment into the liquid reaction mixture.

If the conduct of the reaction gives full conversion there is no problem of removing starting materials from the reaction mixture and recirculating the same, and materials separation is therefore enormously simplified. The catalyst can be synthesized from inexpensive precursors by a process which is simple, reproducible and capable of industrial-scale operation. The catalyst can be repeatedly recycled.

The reaction may be carried out without solvent, i.e. in bulk, or in a solvent. Suitable solvents are any organic solvent or mixture of these with water in which the catalyst is stable and which is stable to the catalyst. For example, the active component (heteropolyanion) must not become separated from the support to any significant extent, and the solvent (in particular alcohols) must not itself be oxidized under the reaction conditions selected, and the solvent must not react with the alcohol starting material (e.g. acids giving esters) or with reaction products (e.g. anhydrides with water to give acid). Examples of suitable solvents are benzene, alkylated aromatics, in particular toluene, xylenes, chlorinated and fluorinated $C_1$–$C_{10}$ alkanes and aromatics, dichloroethane, chlorobenzenes, in particular monochlorobenzene, o- or m-dichlorbenzene, benzonitrile, alkanecarboxylic acids, in acetate, liquid alkanes and cycloalkanes, e.g. decane, acetonitrile, benzonitrile, DMF, dimethylacetamide, dimethyl sulfoxide (DMSO), alkylated naphthalenes, alkylated biphenyls, decalin, tetralin, diphenylmethane, silicone oils and mixtures of these with water. Particularly suitable solvents for the dimethyl compound are chlorobenzene, dichlorobenzenes, ethyl acetate or butyl acetate.

The catalyst used for the novel process is known from the literature (Fujibayashi, Nakayama, Hamamoto, Sakaguchi, Nishiyama, Ishii, J. Mol. Catal. A 110 (1996) 105–117). This literature is expressly incorporated herein by way of reference. The active component is a NPVMo/C catalyst or an active-carbon-supported ammonium molybdatovanadophosphate. Very generally, the catalyst is composed of a heteropolyoxometallate anion comprising the elements P, V, MO and an alkali metal, alkaline-earth metal and/or ammonium as counter ion, preferably ammonium, on an active-carbon support. 12-Metallophosphates are preferred.

1.) The oxidation of activated alcohols with benzylic or allylic protons at low temperatures of <120° C. is now described.

Heteropolyanions belong to the class of polyoxometallates and exist in an almost infinite variety. The best known members of the group have Keggin structure typically featuring an atom of the 3rd, 4th or 5th main group (e.g. B, Si, P, As) surrounded tetrahedrally by $M_3O_{10}$ units (M=Mo, W) which, in turn, are linked to one another via oxygen atoms. The general empirical formula is $H_3XM_{12}O_{40}$. In addition to these there are also a wide variety of defect structures and larger aggregates, e.g. Dawson-type heteropolyacids. The tungsten-containing heteropolyacids in particular feature high acid strength, while the molybdenum-containing heteropolyacids also have pronounced redox properties. Molybdenum and tungsten can replace one another and also be replaced by other metals, e.g. Nb or V. This and the choice of the appropriate heteroatom permit the various properties of the heteropolyacids to be controlled as desired. In addition, other modifications to properties can be achieved by substituting metal ions for the protons. Heteropolyphosphoric acids particularly suitable for the present invention are those of molybdenum in which much of the molybdenum has been substituted by vanadium. This substitution lowers the pKa and increases the susceptibility of the heteropolyacid to reduction. At a degree of substitution of up to 3 the synthesis gives particular Keggin-type heteropolyacids. At the degree of substitution prevailing in the present invention, however, no definite compound is obtained, but rather a complicated mixture of positional, substitutional and structural isomers of the molybdatovanadophosphate.

A particularly suitable compound for the present invention is an ammonium molybdatovanadophosphate obtained from $NaVO_3$ and $Na_2MoO_4$ by adding $H_3PO_4$ and introducing the aqueous solution into $NH_4Cl$ solution, and isolating and purifying the precipitate. This active component is then applied to the active-carbon support by saturation. Active-carbon supports are known low-cost supports for noble metals and, due to their large internal surface area, are known adsorbents. The internal surface is generally occupied by functional groups which can give the active carbon either acid or basic properties. Some active carbons have a proportion of heteroatoms (O, N, H) which can be more than 10% by weight. Depending on their preparation, active carbons may be microporous or else mesoporous.

Active-carbon supports particularly suitable for the present invention are those which have been chemically activated and feature a high proportion of large pores, and the internal surface area of these is therefore markedly less than from 1400 to 1600 $m^2/g$. They are typically obtained from water-vapor-activated microporous active carbons. Among the active carbons tested, particularly successful types are those whose BET surface area is in the range from 500 to 1500 $m^2/g$, preferably from 1000 to 1400 $m^2/g$. The pH of the active-carbon supports may be from 1 to 10, preferably from 2to6. The support may be blended with other (inert) components, binders and additives and be utilized in the form of pellets, beads, tablets, rings, strands, stars or other moldings, or as granules, paste or powder. The diameter or the length and thickness of the molded supports is generally from 1 to 10 mm. However, for the suspension method in the liquid phase no moldings are needed, but powders, pastes or granules may, of course, still be used.

Other metals and nonmetals may also be used to promote or dope the catalyst.

The NPVMo loading of the catalyst is generally in the range from 1 to 25% by weight, preferably in the range from 3 to 15% by weight. The required loading can be applied in one step or by multiple deposition.

To apply the heteropolyanion to the active-carbon support use may be made of the usual processes, such as saturating, impregnating, dipping or spray-impregnating.

The novel process features in particular high conversions simultaneously with good selectivity. Specifically, the selectivity of the reaction after 100 hours is ≧90% at a conversion of >90%.

The examples below are intended to illustrate the invention.

EXAMPLE 1

Preparation of the Catalyst

1) Preparation of the NPVMo Active Component 14.64 g of sodium metavanadate $NaVO_3 \cdot H_2O$ are charged to a 250 ml multinecked flask, dissolved in 76 ml of bidistilled water and stirred to give a milky solution.

16.4 g of sodium molybdate dihydrate $Na_2MoO_4 \cdot 2H_2O$ are dissolved in 24 ml of bidistilled water and then added to the $NaVO_3$ solution, and stirring is continued for 10 min.

A solution of 15.2 g of $H_3PO_4$ (85%) in 20 ml of bidistilled water is slowly added dropwise via a 50 ml dropping funnel. A yellow coloration immediately appears and changes to dark red toward the end of the dropwise addition.

Stirring is continued for 1 h at 95° C. and the mixture is allowed to stand overnight.

The contents of the flask are stirred into 300 ml of a saturated ammonium chloride solution, giving a brown precipitate. This precipitate is filtered off through a glass suction filter and then purified twice using 0.25 molar $H_2SO_4$ (50 ml). The precipitate is dried overnight in a drying cabinet.

2.) Applying the NPVMO Active Component to an Active-Carbon Support

The active-carbon support used in the examples has a BET specific surface area of 1300 $m^2/g$ and a pH of 4. 12 g of the abovementioned active composition are mixed with 400 ml of distilled water and stirred for 2 h at room temperature. This solution is then filtered to give a clear red solution. 108 g of active carbon are added to this red solution and the mixture is stirred for 4 h at room temperature, then filtered via a suction filter. The black powder is dried in a drying cabinet.

EXAMPLE 2

Laboratory Autoclave Experiment (Experiment 20)

0.38 g=2.5 mmol of 1,5-dimethylbicyclo[3.2.1]octan-8-ol starting material in 10 ml of chlorobenzene solvent are charged with 250 mg of catalyst to a 100 ml Roth laboratory autoclave with magnetic stirrer (giving 90 ml of gas space) and once the reaction temperature of 150° C. has been achieved synthetic air is applied under pressure at 15 bar. During the course of the reaction the pressure in the autoclave falls due to consumption of the air. The duration of the reaction is 15 h. No further air is introduced, i.e. the amount of oxygen is limited. With air at 15 bar (=3 bar of $O_2$) and 150° C. the amount of oxygen charged is about 7.7 mmol, i.e. there is an approximately 3-fold molar excess of oxygen.

An HP 5890 GC with Supelco 2-5358 capillary column (105 m×0.53 mm, 3 mm film, isothermal 145° C.) was used for analysis. The analysis was only qualitative, i.e. the conversion and yields given below have been calculated from the integrated peak areas without correction/quantitative calibration.

The results of the catalyst tests are given in Table 1.

EXAMPLES EXPERIMENTS 14 to 88

Further Laboratory Autoclave Experiments

The autoclave experiments are carried out in a Roth 100 ml autoclave or in a Berkhoff 200 ml autoclave with Teflon lining. Both reactors have a magnetic stirrer.

The experimental procedure is the same as that in Example 2 except that reaction conditions, concentrations, solvents and process details were different in each case, and these can be found in Table 1 together with the results obtained (yield, conversion and selectivity in GC area %).

If the reaction temperature is lowered below 150° C. the reaction rate falls dramatically.

Higher reaction temperatures in the range from 180 to 220° C. allow the reaction rate to rise markedly and therefore the duration of the reaction to be reduced without sacrificing selectivity. These higher-temperature experiments are listed again in Table 5.

The experiments with varying starting material quantities and catalyst quantity are summarized again in Tables 3 and 4.

Selectivity can be further improved by varying the process to maintain a local shortage of oxygen at the active center of the catalyst. The pressure here can be reduced to <10 bar.

Continuous or else discontinuous afterfeed of oxygen at low pressures or even at atmospheric pressure has proven advantageous.

EXAMPLES 89 TO 83

Laboratory Reflux Apparatus Version at Atmospheric Pressure

The experiments at atmospheric pressure were carried out in a reflux apparatus composed of multinecked flask with magnetic stirrer, gas feed pipe, internal thermometer and rapid-cooling unit with continuous oxygen/air feed under atmospheric pressure. The gas feed was controlled via an MFC with a gas flow of 2.5 l/h. The solvent volume was 50 ml.

The results of the catalyst tests are found in FIGS. 1–5.
Pure Oxygen as Oxidizing Agent FIGS. 1 and 2 show the progress of the oxidation in chlorobenzene or butyl acetate as solvent. It can be seen that in chlorobenzene complete conversion is achieved in 70 h, while selectivity is about 90%. The only significant GC byproduct (RT=31.3 in chlorobenzene) does not appear until 30 h have passed and then increases continuously to about 2%. The concentration of this byproduct as a function of time suggests two versions of the process for industrial use, specifically high selectivity with partial conversion or full conversion, avoiding removal of starting material from the reaction mixture.

In butyl acetate only 50 h are required for full conversion to be reached. The byproduct is already present at the start of the reaction and increases approximately linearly to about 6% as the reaction progresses. Since further byproduct continues to be formed at 100% conversion it may be concluded that this is produced by a follow-on reaction from product already formed (presumably further oxidation of the ketone with ring-opening of the bicyclic system). There is also a conclusion for the industrial conduct of the reaction: that the reaction must be terminated at the correct juncture (shortly after reaching full conversion) to avoid unnecessary selectivity losses.
Air Oxidation FIG. 3 shows the progress of air oxidation at atmospheric pressure (gas flow 2.5 l/h of air) in chlorobenzene.

After 70 h conversion is 100% and selectivity is greater than >95%. FIG. 4 shows the progress of air oxidation at atmospheric pressure (gas flow 2.5 l/h of air) in butyl acetate. After 80 h conversion is 100% and selectivity is greater than >90%.

Selectivity can therefore be increased by using air instead of pure $O_2$.

FIG. 5 shows the progress of air oxidation at atmospheric pressure (gas flow 2.5 l/h of air) in chlorobenzene with a 3-fold increase in catalyst quantity and starting material quantity. Full conversion is achieved after 55 h at a selectivity of >95%. The starting material quantity and alcohol quantity may therefor then be increased without difficulty by a factor of two or three. Higher concentrations are desirable since they simplify the subsequent treatment of the materials (Experiment 90).

EXAMPLE 84

Pilot Plant Experiments in a 1 l Autoclave (Scale-Up Experiments)

Two experiments (each with different starting material/catalyst concentrations) were carried out in a 1 liter autoclave in a high-pressure pilot plant. In each case the initial charge was 400 g of chlorobenzene and use was made of for Experiment 77: 14 g of cat+15.2 g of alcohol for Experiment 78: 28 g of cat+30.4 g of alcohol (doubled cat/alcohol quantity)

at 150° C. and with lean air (10% $O_2$) at 2.5 bar with a gas flow of 50 l/h and with mechanical stirring at 600 rpm. The product was not isolated, but the reaction mixture was simply analyzed by GC.

The results obtained are even better than in the laboratory autoclave experiments. Experiment 77 (using standard concentrations of cat/alcohol) gives full conversion with 91% selectivity (based on GC area %) after only 24 h, whereas the laboratory apparatus operated at atmospheric pressure had required 70 h, i.e. the duration of the reaction can be further dramatically reduced by optimizing mixing (gas flow, stirrer rotation rate).

A simultaneous two-fold increase in catalyst concentration and alcohol concentration gives a further reduction in the duration of the reaction to 15 h, without loss of selectivity.

Tables 2 and 3 again show results from Experiments 77 and 78.

EXAMPLE 85

Scale-Up Experiment in a 4 Liter Stirred Flask

FIG. 6 shows the progress of the air oxidation in a mechanically stirred reflux apparatus with a 4 liter flask, operated at atmospheric pressure (Experiment 100, 1 kg of chlorobenzene, 70 g of catalyst, 76 g of alcohol, 150° C., gas flow 7.5 l/h of synthetic air). 100% conversion and >95% selectivity are achieved after 50 h.

Table 1: Laboratory Autoclave Experiments
Results of Catalytic Oxidation of 1,5-dimethylbicyclo[3.2.1]octan-8-ol to the Ketone.
Yields and Selectivities in GC Area %

BRIEF DESCRIPTION OF DRAWINGS

FIGS. 1–5: Laboratory Reflux Apparatus Version at Atmospheric Pressure
Results From Catalytic Oxidation of 1,5-dimethylbicyclo[3.2.1]octan-8-ol to the Ketone
Yields and Selectivities in GC Area %
FIG. 1: Pure oxygen, chlorobenzene
FIG. 2: Pure oxygen, butyl acetate
FIG. 3: Air, chlorobenzene
FIG. 4: Air, butyl acetate
FIG. 5: Air, chlorobenzene, 3-fold increase in catalyst quantity and starting material quantity
FIG. 6: Scale-up in a 4 liter stirred flask (atmospheric pressure, chlorobenzene, air) (Experiment 100)
Results of the Catalytic Oxidation of 1,5-dimethylbicyclo[3.2.1]octan-8-ol to the Ketone
Tables 2 and 3: Pilot Plant Experiments With Lean Air in a 1 l Autoclave
Results From Catalytic Oxidation of 1,5-dimethylbicyclo[3.2.1]octan-8-ol to the Ketone
Table 2: Experiment 77
Table 3: Experiment 88

TABLE 1

| Exp. No. | Reactor | Solvent | Temperature | Pressure | Time | GC area % | Conversion | Selectivity | Remarks |
|---|---|---|---|---|---|---|---|---|---|
| 1 | Roth | Chlorobenzene | 220° C. | 30 | 4 | 83.6 | 100 | 83.6 | 250 mg cat./385 mg alco./10 ml solv. |
| 2 | Roth | Chlorobenzene | 220° C. | 15 | 15 | 90 | 100 | 90 | 250 mg cat./380 mg alco./10 ml solv. |
| 3 | Roth | Chlorobenzene | 150° C. | 15 | 15 | 95 | 100 | 95 | 250 mg cat./380 mg alco./10 ml solv. |
| 4 | Roth | Acetic acid | 150° C. | 15 | 15 | 51 | 100 | 51 | 250 mg cat./380 mg alco./10 ml solv. |
| 5 | Roth | Toluene | 150° C. | 15 | 15 | 41 | 84 | 48.8 | 250 mg cat./380 mg alco./10 ml solv. |
| 6 | Roth | Methanol | 150° C. | 15 | 15 | 18 | 19 | 94.7 | 250 mg cat./380 mg alco./10 ml solv. |
| 7 | Roth | Ethanol | 150° C. | 15 | 15 | 5 | 5 | 100 | 250 mg/cat./360 mg alco./10 ml solv. |
| 8 | Roth | Ethyl acetate | 150° C. | 15 | 15 | 57 | 60 | 95 | 250 mg cat./380 mg alco./10 ml solv. |
| 9 | Roth | n-Decane | 150° C. | 15 | 15 | 10 | 45 | 22.2 | 250 mg cat./380 mg alco./10 ml solv. |
| 10 | Roth | DMF | 150° C. | 15 | 15 | 11 | 80 | 13.8 | 250 mg cat./380 mg alco./10 ml solv. |
| 11 | Roth | Benzonitrile | 150° C. | 15 | 15 | 15 | 100 | 15 | 250 mg cat./380 mg alco./10 ml solv. |
| 12 | Roth | Dichloroethane | 150° C. | 15 | 15 | 8 | 18 | 44.4 | 250 mg cat./380 mg alco./10 ml solv. |
| 13 | Roth | Acetic acid 10% water | 150° C. | 15 | 15 | 28 | 85 | 32.9 | 250 mg cat./380 mg alco./10 ml solv. & 1 ml water. |
| 14 | | Chlorobenzene | 150° C. | 15 bar | 15 h | 0% | 0% | 0% | Exp. with only catalyst, no alcohol |
| 15 | | Chlorobenzene | 100° C. | 15 bar | 15 h | 4.86% | 13.35% | 36.40% | Berghof autoclave, solv. = colorless |
| 16 | | Chlorobenzene | 150° C. | 15 bar | 15 h | 71.64% | 81.80% | 87.60% | Berfhof autoclave, solv. = yellowish |
| 17 | | Chlorobenzene | 125° C. 150° C. | 0 bar | 5 h 39 h | from 3.21% to 66.67% | from 8.32% to 69.94% | from 38.58% to 95.32% | Glass app at atm. pres., in 1 terminated due to flask failure |
| 18 | | Chlorobenzene | 160° C. | 15 bar | 10 h | 75.00% | 87.59% | 85.60% | Berghof autoclave, solv. = yellowish |
| 19 | | Chlorobenzene | 160° C. | 10 bar | 15 h | 76.39% | 84.48% | 90.40% | Small autoclave, solv. = yellowish |
| 20 | | Chlorobenzene | 150° C. | 15 bar | 15 h | 79.06% | 90.00% | 87.80% | Small autoclave as described in Example 2 with only 10 ml of solv. |
| 21 | | Chlorobenzene | 160° C. | 15 bar | 10 h | 70.62% | 93.58% | 75.50% | Berghof autoclave/doubled quantity of cat. & octanol with 20 ml of solv. |
| 22 | | Chlorobenzene | 160° C. | 5/10/15 bar | 3/6/9 h | 69.01% | 76.05% | 90.74% | Berghof autoclave, as Exp. 17 |
| 23 | | Chlorobenzene | 150° C. | 10 bar | 15 h | 85.83% | 97.52% | 88.00% | Small autoclave/but with more cat. 375 mg of cat./380 mg of alcohol/10 ml of solv. |
| 24 | | Chlorobenzene | 160° C. | 10 bar | 5 h/ 10 h | 61.22%/ 71.30% | 69.09%/ 96.99% | 88.61% 73.51% | Berghof/doubled amount of cat. & alco. sample after 5 h/ cat./then further 5 h |
| 25 | | Chlorobenzene | 140° C. | 15 bar | 15 h | 76.09% | 85.82% | 88.66% | Small autoclave/as Exp. 20 temp. 10° C. lower |
| 26 | | Chlorobenzene | 150° C. | 8 bar | 15 h | 83.84% | 92.04% | 91.09% | Small autoclave/but with more cat. 375 mg of cat./380 mg of alco./10 ml of solv. |

TABLE 1-continued

| Exp. No. | Reactor | Solvent | Temperature | Pressure | Time | GC area % | Conversion | Selectivity | Remarks |
|---|---|---|---|---|---|---|---|---|---|
| 27 | | Chlorobenzene | 160° C. | 7 bar | 15 h | 73.23% | 92.73% | 78.97% | Berghof/doubled amount of cat. & alco. As Exp. 23 but 15 h |
| 28 | | Chlorobenzene | 150° C. | 6 bar | 15 h | 80.00% | 86.28% | 92.72% | Small autoclave/but with more cat. 375 mg of cat./380 mg of alco./10 ml of solv. |
| 29 | | Chlorobenzene | 140/150/160 | 8 bar 3 bar | 5 h/10 h 15 h | 70.07% | 81.47% | 86.00% | Berghof/doubled amount of cat. & alco. Temperature gradient |
| 30 | | Chlorobenzene | 160° C. | 5 bar | 15 h | 68.79% | 82.67% | 83.21% | Berghof/as Exp. 27 but lower pressure |
| 31 | | Chlorobenzene | 150° C. | 6 bar | 20 h | 84.56% | 92.22% | 91.69% | Small autoclave/as Exp. 28 but 5 h longer |
| 32 | | Chlorobenzene | 150° C. | 8 bar | 15 h | 80.60% | 88.10% | 91.49% | Small autoclave/but with more cat. As Exp.26 but with new cat. charge |
| 33 | | Chlorobenzene | 150° C. | atm. pres. | 78 h | 92.70% | 98.59% | 94.03% | As 16 but with doubled amount of cat., & alco., with 50 ml of chlorobenzene |
| 34 | | Chlorobenzene | 150° C. | 10 bar/ 7 bar 4 bar | 5 h/10 h 15 h | 82.80% | 89.89% | 92.11% | Small autoclave/but with more cat. pressure gradient |
| 35 | | Chlorobenzene | 150° C. | 5 bar post regul. | 15 h | 20.80% | 26.89% | 77.35% | Büchi autoclave/Lab. 209/ 1250 mg cat./1900 mg alco./ 50 ml of chlorobenzene |
| 36 | | Toluene | 150° C. | 10 bar | 15 h | 52.90% | 64.31% | 82.26% | Berghof/20 ml of toluene/250 mg of cat. 380 mg of alcohol/ |
| 37 | | Toluene | 150° C. | 5 bar | 15 h | 48.43% | 57.51% | 84.21% | Berghof/Autoclave// 250 mg of cat. & 380 mg of alco. & 20 ml of t |
| 38 | | Toluene | 150° C. | 10 bar | 15 h | 59.64% | 69.34% | 86.01% | Roth autoclave//250 mg of cat. & 380 mg of alco. & 10 ml of t |
| 39 | | Ethyl acetate | 150° C. | 10 bar | 15 h | 84.10% | 92.55% | 90.87% | Berghof/Autoclave// 250 mg of cat. & 380 mg of alco. & 20 ml of ea |
| 40 | | Ethyl acetate | 150° C. | 8 bar | 15 h | 57.14% | 62.19% | 91.88% | Roth autoclave//as Exp. 26 375 mg of cat. & 380 mg of alco. & 10 ml ea |
| 41 | | Ethyl acetate | 150° C. | 5 bar | 15 h | 56.33% | 62.90% | 89.55% | Berghof/Autoclave// 250 mg of cat. & 380 mg of alco. & 20 ml of ea |
| 42 | | Chlorobenzene | 150° C. | 8 bar | 15 h | 81.82% | 88.45% | 92.50% | Roth autoclave as Exp. 22 cat. test batch 2 & 3 |
| 43 | | Ethyl acetate | 150° C. | 15 bar | 15 h | 69.05% | 76.98% | 89.70% | Roth autoclave // as Exp. 40 375 mg of cat. & 380 mg of alco. & 10 ml of ea |
| 44 | | Chlorobenzene | 160° C. | 8 bar | 15 h | 75.08% | 94.02% | 79.86% | Berghof/Autoclave//as 30 bar increased 500 mg of cat. & 760 mg of alco. & 20 ml of chlorobenzene |
| 45 | | Chlorobenzene | 150° C. | 10 bar | 15 h | 12.78% | 19.21% | 66.53% | Büchi autoclave/repeat of 35 1.25 g of cat./1.9 g of alco./ 50 ml of chlorobenzene |
| 46 | | Chlorobenzene | 150° C. | 10 bar | 15 h | 66.02% | 77.64% | 85.03% | Berghof/Autoclave//conc. increase 500 mg of cat. & 760 mg of alco. & 20 ml of ch |
| 47 | | Chlorobenzene | 150° C. | 10 bar | 15 h | 48.81% | 55.76% | 87.54% | Roth autoclave//conc. increase 500 mg of cat. & 760 mg of alco. & 10 ml of ch |
| 48 | | Butyl Acetate | 150° C. | atm. pres. | 71.5 h | 91.94% | 100% | 91.94% | Glass app. 1250 mg of cat./1900 mg of alco./50 ml of ba |
| 49 | | Chlorobenzene | 150° C. | 10 bar | 15 h | 51.51 | 59.08 | 87.19 | Roth autoc. Exp. with used cat. from Exp. 33/250 mg of cat./380 mg of alco. |
| 50 | | Butyl acetate | 150° C. | 10 bar | 15 h | 79.29 | 91.7 | 86.47 | Berghof/Autoclave//butyl acetate solv. 250 mg of cat./ 380 mg of alco./20 ml of solv. |
| 51 | | Chlorobenzene | 150° C. | 10 bar | 15 h | 75.93 | 84.55 | 89.8 | Roth autoc. Exp. with used cat. 375 mg of cat./380 mg of alco./10 ml of ch |

TABLE 1-continued

| Exp. No. | Reactor | Solvent | Temperature | Pressure | Time | GC area % | Conversion | Selectivity | Remarks |
|---|---|---|---|---|---|---|---|---|---|
| 52 | | Butyl acetate | 160° C. | 8 bar | 15 h | 71.33 | 79.9 | 89.27 | Berghof/Autoclave//as 44/low bar 500 mg of cat. & 760 mg. of alco. & 20 ml of ba |
| 53 | | Chlorobenzene | 150° C. | 10 bar | 15 h | 68.73 | 77.83 | 88.31 | Berghof/Autoclave//250 mg of cat./380 mg of alco./20 ml of solv. |
| 54 | | Acetic acid 100% | 150° C. | 10 bar | 15 h | 39.15 | 98.98 | 39.55 | Roth autoclave 250 mg of cat./380 mg of alco./10 ml of solv. |
| 55 | | Acetic acid 100% | 150° C. | 15 bar | 15 h | 43.1 | 99.33 | 43.39 | Roth Autoclave 250 mg of cat./380 mg of alco./10 ml of solv. |
| 56 | | Chlorobenzene | 150° C. | 10 bar | 15 h | 45.36 | 48.83 | 92.89 | Büchi Autoclave 250 mg of cat./380 mg of alco./20 ml of solv. |
| 57 | | Acetic anhydride | 150° C. | 10 bar | 15 h | 16.43 | 100 | 16.43 | Berghof Autoclave 375 mg of cat./380 mg of alco./20 ml of solv. |
| 58 | | Acetic anhydride | 150° C. | 15 bar | 15 h | 11.33 | 100 | 11.33 | Berghof Autoclave 375 mg of cat./380 mg of alco./20 ml of solv. |
| 59 | | Acetic anhydride | 150° C. | 10 bar | 15 h | 10.03 | 100 | 10.03 | Roth Autoclave 250 mg of cat./380 mg of alco./10 ml of solv. |
| 60 | | Acetic anhydride | 150° C. | 8 bar | 15 h | 15.79 | 100 | 15.79 | Berghof Autoclave 375 mg of cat./380 mg of alco./20 ml of solv. |
| 61 | | Chlorobenzene | 150° C. | 0 bar | 79 | 94.4 | 100 | 94.4 | Glass app., synth. air 1250 mg of cat./1900 mg of alco./50 ml of solv. |
| 62 | | Acetic anhydride | 150° C. | 15 bar | 15 h | 9.82 | 100 | 9.82 | Roth autoclave 250 mg of cat./380 mg of alco./10 ml of solv. |
| 63 | | Chlorobenzene | 150° C. | 8 bar | 15 h | 35.16 | 100 | 35.16 | Roth autoc. as Exp. 26 1st cat. test Batch IV. |
| 64 | | Ethylene glycol experiments Chlorobenzene | 150° C. | 10 bar | 15 h | | | | Berghof autoclave 150 mg of et. glycol/250 mg of cat./10 ml of solv. |
| 65 | | Chlorobenzene | 150° C. | 8 bar | 15 h | 84.03 | 98.33 | 85.46 | Roth autoc. as Exp. 26 150 mg of et. clycol/250 mg of cat./10 ml of solv. |
| 66 | | Ethylene glycol experiments Chlorobenzene | 150° C. | 10 bar | 15 h | | | | Repeat of Exp. 26 |
| 67 | | Ethylene glycol experiments Chlorobenzene | 150° C. | 10 bar | 15 h | | | | Roth autoclave 150 mg of et. glycol/250 mg of cat./20 ml of solv. |
| 68 | | Ethylene glycol experiments Chlorobenzene | 160° C. | 10 bar | 15 h | | | | Berghof autoclave 150 mg of et. glycol/250 mg of cat./20 ml of solv. |
| 69 | | Chlorobenzene | 150° C. | 8 bar | 15 h | 88.27 | 97.89 | 90.17 | Roth autoc. as Exp. 26 3rd cat. test Batch IV. |
| 70 | | Chlorobenzene | 150° C. | 15 bar | 15 h | 72.75 | 89.11 | 81.64 | Berghof autclave/Conc. increase 500 mg of cat./760 mg of alco./20 ml of solv. |
| 71 | | Butyl acetate | 150° C. | 0 bar | 85 h | 89.96 | 100 | 89.96 | Glass app., synth. air 1250 mg of cat./1900 mg of alco./50 ml of ba |
| 72 | | Chlorobenzene | 150° C. | 3 × 8 bar | 3 × 5 h | 76.14 | 90.28 | 84.54 | Berghof autoclave/conc. increase 300 mg of cat./760 mg of alco./10 ml of solv. |
| 73 | | Chlorobenzene | 150° C. | 10 bar | 15 h | 47.65 | 54.2 | 87.91 | Roth autoclave/conc. increase 300 mg of cat./760 mg of alco./10 ml of solv. |
| 74 | | o-Xylene | 150° C. | 10 bar | 15 h | 69.92 | 74.66 | 93.65 | Roth autoclave//375 mg of cat./380 mg of alco./10 ml of solv. |
| 75 | | o-Xylene | 150° C. | 8 bar | 15 h | 44.70 | 73.62 | 60.71 | Roth autoclave//375 mg of cat./380 mg of alco./10 ml of solv. |
| 76 | | Chlorobenzene | 150° C. | 8 bar | 1 × 10 h<br>1 × 5 h | 54.45<br>74.96 | 60.65<br>87.33 | 89.78<br>85.84 | Berghof autoclave//as Exp. 72 500 mg of cat./760 mg of alco./20 ml of solv. |
| 77 | | Chlorobenzene | 150° C. | 2.5 bar | 24 h | 90.97 | 100 | 90.97 | 1 Ltr. autoclave in pilot plant 400 g of solv/14 g of cat./15.2 g of alco. |

TABLE 1-continued

| Exp. No. | Reactor Solvent | Temperature | Pressure | Time | GC area % | Conversion | Selectivity | Remarks |
|---|---|---|---|---|---|---|---|---|
| 78 | Chlorobenzene | 150° C. | 8 | 15 h | 48.35 | 54.54 | 88.65 | Roth autoclave//500 mg of cat./760 mg of alco./10 ml of solv. |
| 79 | Chlorobenzene | 150° C. | 15 | 15 h | 68.40 | 86.65 | 78.94 | Berghof autoclave//3× conc. 750 mg of cat./1.14 g of alco./20 ml of solv. |
| 80 | No solvent | 150° C. | 10 | 15 h | 8.61 | 17.88 | 48.15 | Roth autoclave//375 mg of cat./5 g of alco. |
| 81 | Chlorobenzene | 150° C. | 0 | 69 h | 94.5 | 100 | 94.5 | Glass app//2.5 g of cat./3.8 g of alco./50 ml of solv. |
| 82 | Chlorobenzene | 220° C. | 25 | 2 h | 92.15 | 100 | 92.15 | Roth autoclave//250 mg of cat./385 mg of alco./10 ml of solv. |
| 83 | Chlorobenzene | 150° C. | 15 | 15 h | 73.17 | 83.18 | 87.97 | Roth autoclave//as Exp. 78 doubled conc. |
| 84 | Chlorobenzene | 150° C. | 15 | 15 h | 64.89 | 94.91 | 68.37 | Berghof autoclave//as Exp. 79 but more cat. 1 g of cat./1.14 g of alco./20 ml of solv. |
| 85 | No solvent | 150° C. | 15 | 15 h | 11.58 | 20.02 | 57.84 | Roth autoclave//as Exp. 80 at higher pressure//5 g of alco./385 mg of cat. |
| 86 | Decalin | 150° C. | 15 | 15 h | 57.18 | 81.15 | 70.46 | Berghof autoclave//new solv. 250 mg of cat./380 mg of alco./20 ml of decalin |
| 87 | Chlorobenzene | 220° C. | 20 | 2 h | 87.44 | 94.74 | 92.29 | Roth autoclave as Exp. 82 |
| 88 | Chlorobenzene | 150° C. | 2.5 bar | 15 h | 91.77 | 100 | 91.77 | 1 Ltr. autoclave in pilot plant as Exp. 77 but doubled conc. |
| 89 | Diphenylmethane | 150° C. | 15 | 15 h | 17.64 | 97.3 | 18.13 | Berghof autoclave//new solv. 250 mg of cat./380 mg of alco./20 g of solv. |
| 90 | Chlorobenzene | 150° C. | 0 | 55 h | 96.93 | 100 | 96.93 | Glass app.//3.75 g of cat./5.7 g of alco./50 ml of solv. |
| 91 | Chlorobenzene | 220° C. | 15 | 2 h | 70.76 | 70.76 | 100 | Roth autoclave |
|   |   |   |   | 4 h | 79.59 | 83.46 | 95.36 | 250 mg/380 mg/10 ml of solv. |
| 92 | Chlorobenzene | 150° C. | 8 | 15 | 57.7 | 96.82 | 58.94 | Berghof autoclave/ 500 mg of cat./380 mg of alco./20 ml of solv. |
| 93 | Chlorobenzene | 150° C. | 15 | 15 | 62.26 | 97.89 | 63.6 | Berghof autoclave/ 750 mg of cat./760 mg of alco./20 ml of solv. |
| 94 | Chlorobenzene | 200° C. | 25 | 2 h | 86.02 | 92.32 | 93.17 | Roth autoclave 250 mg/380 mg/10 ml of solv. |
| 95 | Chlorobenzene | 150° C. | 10 | 15 | 10.24 | 12.95 | 79.09 | Berghof autoclave/new support 750 mg of HAAL0001/ 380 mg of alco./20 ml of a |
| 96 | Chlorobenzene | 200° C. | 20 | 2 h | 89.44 | 96 | 93.17 | Roth autoclave 250 mg/380 mg/ 10 ml of solv. |
| 97 | Chlorobenzene | 180° C. | 25 | 2 h | 81.67 | 87.4 | 93.44 | Roth autoclave 250 mg/380 mg/10 ml of solv. |
| 98 | Chlorobenzene | 150° C. | 10 | 15 | 14.61 | 14.61 | 100 | Berghof autoclave/new support 1500 mg of HAAL0001/ 380 mg of alco./20 ml of s |
| 99 | 1,2-Dichlorobenzene | 150° C. | 8 | 15 | 84.07 | 90.17 | 93.24 | Roth autoclave//new solv. 375 mg of cat./380 mg of alco./10 ml of a |
| 100 | Chlorobenzene | 150° C. | 0 |  |  |  |  | 4 Ltr. glass app.//1000 g of solv.: 70 g of cat./76 g of alcohol |
| 101 | 1,3-Dichlorobenzene | 150° C. | 10 | 15 | 78.46 | 83.56 | 93.9 | Berghof autoclave/new solv. 250 mg/380 mg/20 ml of solv. |
| 102 | 1,3-Dichlorobenzene | 150° C. | 15 | 15 | 76.24 | 85.2 | 89.48 | Berghof autoclave//101 higher pr. 250 mg/380 mg/20 ml of solv. |
| 103 | 1,2-Dichlorobenzene | 180° C. | 8 | 4 | 31.11 | 35.72 | 87.09 | Roth autoclave//higher temp. 375 mg of cat./380 mg of alco./10 ml of s |

TABLE 2

This experiment was carried out in a 1 ltr. autoclave
400 g of solvent/14 g of catalyst/15.2 g of the alcohol

| Solvent | Temperature | Pressure | Time | GC area % | Conversion | Selectivity | Byproduct |
|---|---|---|---|---|---|---|---|
| Chlorobenzene | | | | | | | |
| Chlorobenzene | | | 0 h | | | | |
| Chlorobenzene | 150° C. | 2.5 bar | 3.5 h | 34.64 | 40.12 | 86.34 | 0.36 |
| Chlorobenzene | 150° C. | 2.5 bar | 11 h | 70.79 | 77.98 | 90.78 | 2.90 |
| Chlorobenzene | 150° C. | 2.5 bar | 18 h | 87.25 | 94.2 | 92.62 | 4.02 |
| Chlorobenzene | 150° C. | 2.5 bar | 24 h | 90.97 | 100 | 90.97 | 6.50 |

TABLE 3

This experiment was carried out in a 1 ltr. autoclave
400 g of solvent/28 g of catalyst/30.4 g of the alcohol
(Doubled quantity of starting materials)

| Solvent | Temperature | Pressure | Time | GC area % | Conversion | Selectivity | Byproduct |
|---|---|---|---|---|---|---|---|
| Chlorobenzene | | | | | | | |
| Chlorobenzene | | | 0 h | | | | |
| Chlorobenzene | 150° C. | 2.5 bar | 7.5 h | 67.48 | 72.12 | 93.57 | 3.085 |
| Chlorobenzene | 150° C. | 2.5 bar | 15 h | 91.77 | 100 | 91.77 | 6.53 |

TABLE 4

Concentration Experiments

| | Reactor Berghof = 200 ml Roth = 100 ml | Solv. | Temp. | Pressure | Time | Prod. % | Conversion | Selectivity | Remarks |
|---|---|---|---|---|---|---|---|---|---|
| 46 | Berghof | Chlorobenzene | 150° C. | 10 bar | 15 h | 66.02 | 77.64 | 85.03 | 500 mg of cat./760 mg of alco. & 20 ml of solv. |
| 47 | Roth | Chlorobenzene | 150° C. | 10 bar | 15 h | 48.81 | 55.76 | 87.54 | 500 mg of cat./760 mg of alco. & 10 ml of solv. |
| 52 | Berghof | butyl acetate | 160° C. | 8 bar | 15 h | 71.33 | 79.9 | 89.27 | 500 mg of cat./760 mg of alco. & 20 ml of solv. |
| 70 | Berghof | Chlorobenzene | 150° C. | 15 bar | 15 h | 72.75 | 89.11 | 81.64 | 500 mg of cat./760 mg of alco. & 20 ml of solv. |
| 72 | Berghof | Chlorobenzene | 150° C. | 3 × 8 bar | 3 × 5 h | 76.14 | 90.28 | 84.54 | 500 mg of cat./760 mg of alco. & 20 ml of solv. |
| 73 | Roth | Chlorobenzene | 150° C. | 10 bar | 15 h | 47.65 | 54.2 | 87.91 | 300 mg of cat./760 mg of alco. & 10 ml of solv. |
| 76 | Berghof | Chlorobenzene | 150° C. | 8 bar | 1 × 10 h | 54.45 | 60.65 | 89.76 | 500 mg of cat./760 mg of alco. & 20 ml of solv. |
| | | | | | 1 × 5 h | 74.96 | 87.33 | 85.84 | |
| 78 | Roth | Chlorobenzene | 150° C. | 8 bar | 15 h | 48.35 | 54.54 | 88.65 | 500 mg of cat./760 mg of alco. & 10 ml of solv. |
| 79 | Berghof | Chlorobenzene | 150° C. | 15 bar | 15 h | 68.4 | 86.65 | 78.94 | 750 mg of cat./1140 mg of alco. & 20 ml of solv. |
| 83 | Roth | Chlorobenzene | 150° C. | 15 bar | 15 h | 73.17 | 83.18 | 87.97 | 500 mg of cat./760 mg of alco. & 10 ml of solv. |
| 84 | Berghof | Chlorobenzene | 150° C. | 15 bar | 15 h | 64.89 | 94.91 | 68.37 | 1000 mg of cat./1140 mg of alco. & 20 ml of solv. |
| 92 | Berghof | Chlorobenzene | 150° C. | 8 bar | 15 h | 57.70 | 96.82 | 58.94 | 500 mg of cat./380 mg of alco. & 20 ml of solv. |
| 93 | Berghof | Chlorobenzene | 150° C. | 15 bar | 15 h | 62.26 | 97.89 | 63.6 | 750 mg of cat./760 mg of alco. & ml of solv. |

TABLE 5

Experiments at High Temperature

| No. | Solvent | Temp. | Pressure | Time | % Product | % Conversion | % Select. | Comment |
|---|---|---|---|---|---|---|---|---|
| 82 | Chlorobenzene | 220° C. | 25 | 2 h | 92.15 | 100 | 92.15 | Roth autoclave//250 mg of cat./385 mg of alco./10 ml of solv. |
| 87 | Chlorobenzene | 220° C. | 20 | 2 h | 87.44 | 94.74 | 92.29 | Roth autoclave as Exp. 6.72 |
| 91 | Chlorobenzene | 220° C. | 15 | 2 h | 70.76 | 100 | 100 | Roth autoclave 250 mg/380 mg/10 ml of solv. |
| 94 | Chlorobenzene | 220° C. | 25 | 2 h | 86.02 | 92.32 | 93.17 | Roth autoclave 250 mg/380 mg/10 ml of solv. |
| 96 | Chlorobenzene | 220° C. | 20 | 2 h | 89.44 | 96 | 93.17 | Roth autoclave 250 mg/380 mg/10 ml of solv. |
| 99 | Chlorobenzene | 180° C. | 25 | 2 h | 81.67 | 87.4 | 93.44 | Roth autoclave 250 mg/380 mg/10 ml of solv. |

What is claimed is:

1. A process for preparing a bicyclooctanone which comprises reacting, optionally in the presence of a solvent, a bicyclooctanol with a gaseous, oxygen-containing, oxidizing agent in the presence of a active-carbon supported heteropolymetallate catalyst wherein said catalyst comprises heteropolyoxometallate anions of vanadium, molydenum and phosphorous and alkali-metal, alkaline earth-metal and/or ammonium counter ions on an active-carbon support.

2. The process as claimed in claim 1, where the oxidizing agent used comprises air or lean air.

3. The process as claimed in claim 1, where the process is carried out at a pressure of from 1 to 30 bar.

4. The process as claimed in claim 1, where the process is carried out at atmospheric pressure.

5. The process as claimed in claim 1, where the temperature is in the range from 100 to 300° C.

6. The process as claimed in claim 1, where the reaction mixture is agitated.

7. The process as claimed in claim 1, where 1,5-dialkylbicyclo[3.2.1]octan-8-ol is reacted to give 1,5-dialkylbicyclo[3.2.1]octan-8-one.

8. The process as claimed in claim 7, where the alkyl groups, independently of one another, are a branched or unbranched methyl, ethyl, propyl, butyl, pentyl, hexyl or cyclohexyl radical.

9. The process as claimed in claim 1, where the process is carried out in a solvent.

10. The process as claimed in claim 9, where the solvent used comprises chlorobenzene, dichlorobenzenes or butyl acetate.

11. The process as claimed in claim 1, where the catalyst used comprises an active-carbon-supported ammonium molybdatovanadophosphate.

12. The process as claimed in claim 1, where the active-carbon support has a BET specific surface area in the range from 500 to 1500 $m^2/g$.

13. A process for preparing a bicyclooctanone which comprise reacting, optionally in the presence of a solvent, a bicyclooctanol with a gaseous, oxygen-containing, oxidizing agent on the presence of active-carbon-supported heteropolymetallate catalyst where said catalyst comprises heteropolyoxometallate anions of vanadium, molybdenum and phosphorous and alkali-metal, alkaline earth-metal or ammonium counter ions on an active-carbon support, wherein the selectivity after 100 hours, with respect to the bicyclooctanol, is greater than or equal to 90% at a conversion of greater than 90%.

* * * * *